US010383769B1

(12) United States Patent
Miller

(10) Patent No.: US 10,383,769 B1
(45) Date of Patent: Aug. 20, 2019

(54) EYE COVER WITH AUDIO TRANSMITTER

(71) Applicant: Juanita Miller, Chicago, IL (US)

(72) Inventor: Juanita Miller, Chicago, IL (US)

( * ) Notice: Subject to any disclaimer, the term of this patent is extended or adjusted under 35 U.S.C. 154(b) by 41 days.

(21) Appl. No.: 15/474,348

(22) Filed: Mar. 30, 2017

Related U.S. Application Data

(60) Provisional application No. 62/315,059, filed on Mar. 30, 2016.

(51) Int. Cl.
| *A61F 9/04* | (2006.01) |
| *H04R 1/10* | (2006.01) |
| *G02C 11/00* | (2006.01) |
| *A61M 21/00* | (2006.01) |

(52) U.S. Cl.
CPC .............. *A61F 9/04* (2013.01); *G02C 11/10* (2013.01); *H04R 1/1016* (2013.01); *H04R 1/1033* (2013.01); *H04R 1/1041* (2013.01); *H04R 1/1091* (2013.01); *A61M 2021/0083* (2013.01)

(58) Field of Classification Search
CPC .......... A61F 9/04; A61M 2021/0083; A63B 33/002; A63B 2220/40; A63B 2220/30; A63B 2208/03; A63B 2220/803; H04R 1/1016; H04R 1/1033; H04R 1/1041; H04R 1/1091; H04R 3/00; G02C 11/10
See application file for complete search history.

(56) References Cited

U.S. PATENT DOCUMENTS

| 1,553,010 | A | * | 9/1925 | Terry | G02C 7/16 |
| | | | | | 2/15 |
| 4,856,086 | A | * | 8/1989 | McCullough | A61F 9/029 |
| | | | | | 455/344 |
| 4,882,769 | A | * | 11/1989 | Gallimore | H04B 1/088 |
| | | | | | 455/344 |
| 5,867,580 | A | * | 2/1999 | Anderson | G10H 1/0041 |
| | | | | | 381/61 |
| 6,010,216 | A | * | 1/2000 | Jesiek | H04B 1/385 |
| | | | | | 351/158 |
| D485,854 | S | | 1/2004 | Thomason | |
| 6,961,286 | B1 | | 11/2005 | Alagia | |
| 7,202,774 | B2 | | 4/2007 | Hoyle | |
| 7,878,968 | B2 | | 2/2011 | Wittmann-Price et al. | |
| 8,031,560 | B1 | | 10/2011 | Washington | |
| 8,213,670 | B2 | | 7/2012 | Lai | |
| 2001/0019050 | A1 | * | 9/2001 | Rock | D04B 1/04 |
| | | | | | 219/545 |
| 2002/0138891 | A1 | * | 10/2002 | Spiteri | A61F 9/04 |
| | | | | | 2/15 |
| 2005/0046549 | A1 | * | 3/2005 | Hoyle | A61F 9/04 |
| | | | | | 340/309.16 |
| 2006/0034478 | A1 | * | 2/2006 | Davenport | H04R 5/0335 |
| | | | | | 381/381 |
| 2006/0106276 | A1 | * | 5/2006 | Shealy | A61M 21/00 |
| | | | | | 600/27 |

(Continued)

FOREIGN PATENT DOCUMENTS

CN 202982386 U * 6/2013

*Primary Examiner* — Davetta W Goins
*Assistant Examiner* — Kuassi A Ganmavo
(74) *Attorney, Agent, or Firm* — Cramer Patent & Design, PLLC; Aaron R. Cramer

(57) ABSTRACT

An eye cover includes ear plugs integrated into the head strap to transmit audio signals. The audio portion of the device is battery-operated and preprogrammed with a variety of sounds traditionally considered emotionally soothing.

11 Claims, 3 Drawing Sheets

(56) References Cited

U.S. PATENT DOCUMENTS

| | | | |
|---|---|---|---|
| 2008/0065246 A1* | 3/2008 | Zorkendorfer | G06F 1/163 700/94 |
| 2009/0105524 A1* | 4/2009 | Bressler | A61M 21/00 600/27 |
| 2010/0045928 A1* | 2/2010 | Levy | H04M 1/05 351/158 |
| 2011/0249826 A1* | 10/2011 | Van Leest | G10K 11/178 381/71.8 |
| 2013/0063557 A1* | 3/2013 | Saigo | H04N 13/341 348/42 |
| 2013/0184516 A1* | 7/2013 | Genereux | A61M 21/02 600/28 |
| 2013/0255697 A1 | 10/2013 | Thompson | |
| 2013/0278886 A1 | 10/2013 | Vollet | |
| 2014/0253866 A1* | 9/2014 | Carabajal | G06F 3/011 351/123 |
| 2015/0082515 A1* | 3/2015 | Parziale | A61F 9/04 2/173 |

* cited by examiner

EYE COVER WITH AUDIO TRANSMITTER

RELATED APPLICATIONS

The present invention was first described in and claims the benefit of U.S. Provisional Application No. 62/315,059, filed Mar. 30, 2016, the entire disclosures of which are incorporated herein by reference.

FIELD OF THE INVENTION

The present invention relates generally to an eye cover including an audio transmitter integrated therewith.

BACKGROUND OF THE INVENTION

There are a great deal of people who work at night and sleep during the day. Many of these people often wear eye masks to help block out extraneous light, hopefully leading to a more restful and fulfilling sleep. However, sounds such as traffic, construction, or even family members walking about the home can cause interruptions in sleep which lead not only to tiredness later in the day, but perhaps even chronic health problems as well. These same problems exist for those who are light sleepers, those who may be ill, or even those just trying to catch a brief nap in the middle of the day. Accordingly, there exists a need for a means by which unwanted sound and light can be blocked out while sleeping. The use of the eye cover provides users the ability to sleep without visual or audible interruption in a manner which is quick, easy, and effective.

SUMMARY OF THE INVENTION

In order to achieve the object of providing an eye cover that incorporates an audio transmitter, an object of the present invention is to provide such an eye cover that has an eye shield body soft inner surface and a durable outer surface and having an elastic strap to assist in placing the eye cove over the eyes of a user. In certain embodiments, the eye shield body is a dual-layered construction, where a first layer is constructed out of the soft material and the second layer is constructed out of the durable material. The first and second layers are coextensive is size and shape and bonded together. A pair of headphone speakers are each in electrical communication with a control device that is attached to the elastic strap.

Another object of the invention is to provide such a control device that has a housing with a power switch, a volume control switch, and a sound selector switch and a plurality of programmed amount of audio data that is capable of being selected. In certain embodiments, the power switch and volume control switch are combined. In other embodiments, the sound selector switch, upon subsequent activation, cycles through the plurality of programmed audio data.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
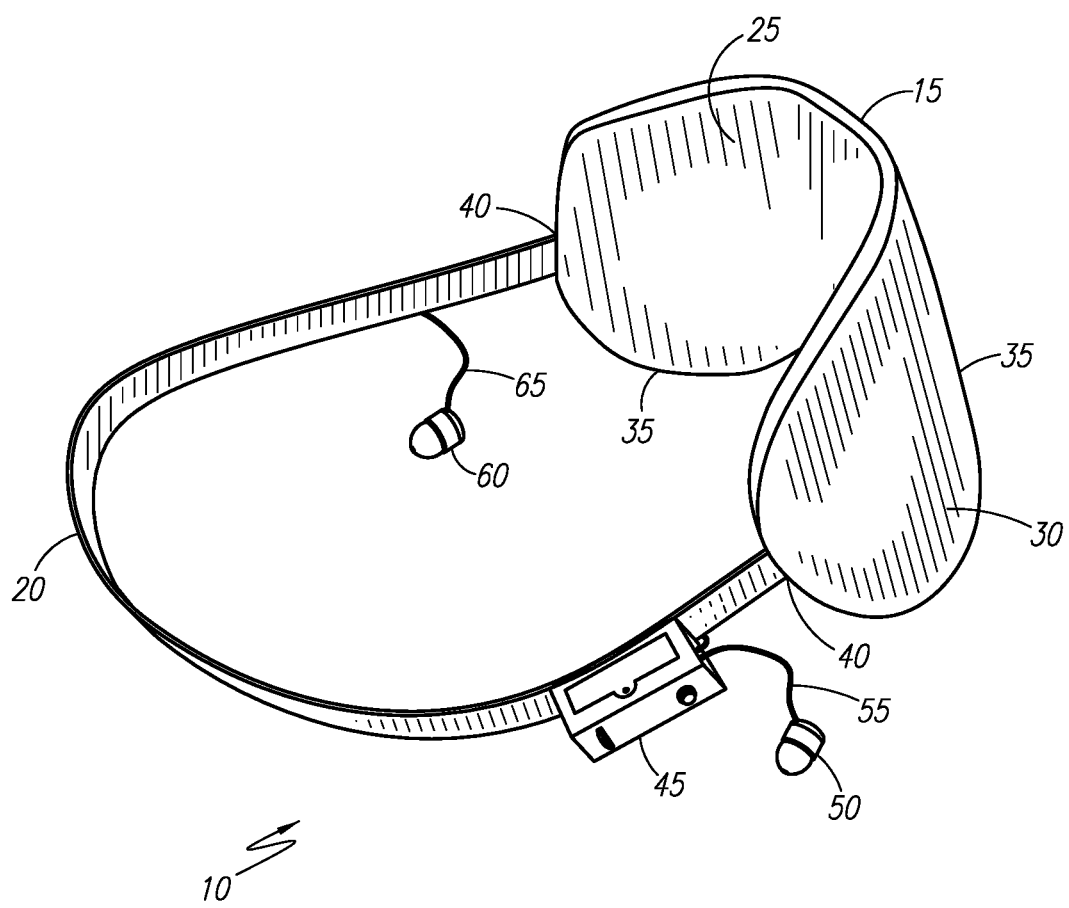
FIG. 1 is an isometric view of the eye cover with audio transmitter 10, according to the preferred embodiment of the present invention.

DESCRIPTIVE KEY 10 eye cover with audio transmitter
15 eye shield
20 elastic strap
25 soft inner surface
30 durable outer surface
35 binding material
40 stitching
45 electronics enclosure
50 right headphone speaker
55 right headphone cable
60 left headphone speaker
65 left headphone cable
70 user
75 eyes
80 nose bridge
85 nose
90 rear head area
95 side surface
100 battery access cover
105 top surface
110 internal user replaceable battery
115 front surface
120 combination ON/OFF switch and volume control
125 sound selector switch
130 ON/OFF switch portion
135 amplifier
140 digital sound circuit with internal memory
145 connecting circuit path
150 potentiometer portion

DETAILED DESCRIPTION OF THE PREFERRED EMBODIMENT

The best mode for carrying out the invention is presented in terms of its preferred embodiment, herein depicted within the FIGS. 1 through 4.

Referring now to FIG. 1, an isometric view of the eye cover with audio transmitter 10, according to the preferred embodiment of the present invention, is disclosed. The eye cover with audio transmitter 10 (herein described as the "apparatus") 10 includes an eye shield 15 and an elastic strap 20. The eye shield 15 comprises a soft inner surface 25 such as terry cloth or satin and a durable outer surface 30 such as nylon or polyester. The soft inner surface 25 and the durable outer surface 30 are preferably coextensive in size and shape and are affixed together (preferably sewn together) with a binding material 35. When in the layered state, the combination of the soft inner surface 25 and the durable outer surface 30 provide almost one hundred percent (100%) of extraneous and unwanted light. The elastic strap 20 is secured to the eye shield 15 by use of stitching 40 or other suitable bonding means. The elastic strap 20 stretches to accommodate users with different head sizes and is suitable for use by men, women, and children. An electronics enclosure 45 is attached to the elastic strap 20 for the purposes of containing the various electronic components as used with the apparatus 10. The internal components of the electronics enclosure 45 along with its operation will be described in greater detail herein below. A right headphone speaker 50 is physically and electrically connected to the electronics enclosure 45 by a right headphone cable 55. Likewise, a left headphone speaker 60 is physically and electrically connected to the electronics enclosure 45 by a left headphone cable 65. The balance of the left headphone cable 65 is routed through the interstitial space between the soft inner surface 25 and the durable outer surface 30 due to its non-stretchable construction. The durable outer surface 30 would be provided in a wide variety of colors such as red, black, white, green, blue, or pink to suit user preferences.

Figure 2:
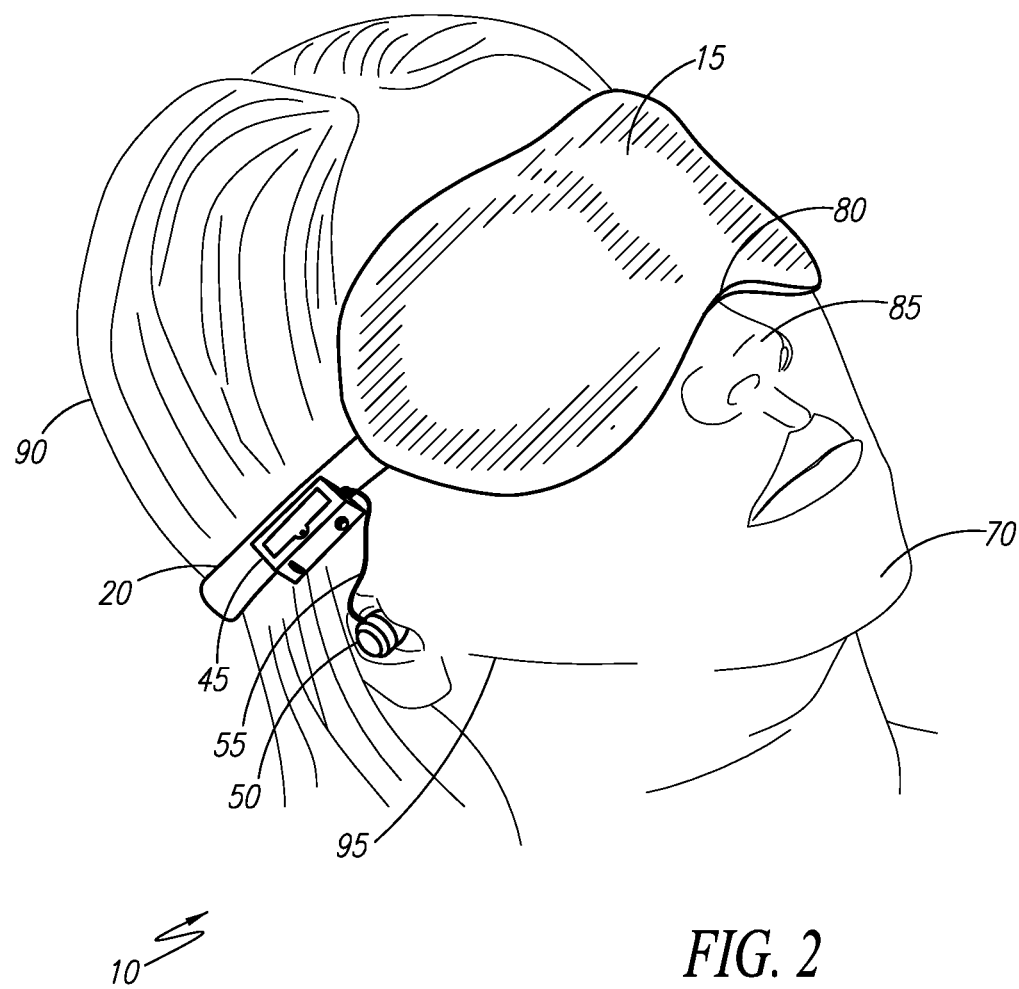
FIG. 2 is an isometric view of the eye cover with audio transmitter 10 shown in a utilized state according to the preferred embodiment of the present invention.

Referring next to FIG. 2, an isometric view of the apparatus 10, shown in a utilized state upon a user 70, according to the preferred embodiment of the present invention is depicted. The eye shield 15 is positioned over the eyes 75 (not shown due to illustrative limitations) of the user 70 with a nose bridge 80 of the eye shield 15 positioned and centered over the nose 85 of the user 70. The elastic strap 20 is routed around a rear head area 90 where its elastic nature maintains a snug, but not constrictive, fit that remains in place as the user 70 moves about in normal sleep patterns. The right headphone cable 55 is shown in place between the electronics enclosure 45 and the right headphone speaker 50 as aforementioned described. The right headphone speaker 50 is placed into the side surface 95 of the user 70. While the right headphone speaker 50 and the left headphone speaker 60 (as shown in FIG. 1) are depicted as "in-ear" devices, it should be noted that other devices such as "on the ear", "behind the ear", or "over the ear" devices would work equally as well, and the inclusion of only one (1) particular type of speaker is not intended to be a limiting factor of the present invention. The utilization mode as depicted in FIG. 2 is intended to depict operation as experienced by those users 70 who may have difficulty falling asleep, those who are awakened easily, those who work night shifts, migraine suffers, or those simply looking to block out the world for a short relaxing nap.

Figure 3:
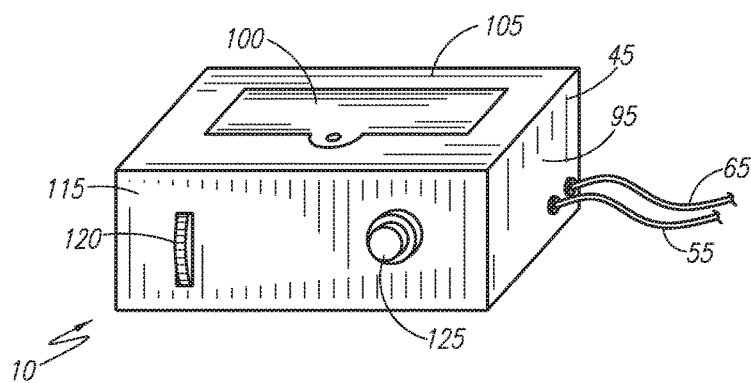
FIG. 3 is a detailed view of the electronics enclosure 45 as used with the eye cover with audio transmitter 10, according to the preferred embodiment of the present invention; and, FIG. 4 is an electrical block diagram depicting the major electrical components of the eye cover with audio transmitter 10, according to the preferred embodiment of the present invention.

Referring now to FIG. 3, a detailed view of the electronics enclosure 45 as used with the apparatus 10, according to the preferred embodiment is shown. The right headphone speaker 50 and the left headphone speaker 60 are shown exiting a side surface 95 of the electronics enclosure 45 where they connect to the right headphone cable 55 (as shown in FIG. 1) and the left headphone cable 65 (as shown in FIG. 1) respectively. A battery access cover 100 is located on the top surface 105 of the electronics enclosure 45. The battery access cover 100 provides access to an internal user replaceable battery 110 (not visible due to illustrative limitations) envisioned to be a size "C" battery. Other sizes and types of batteries including rechargeable versions can also be used and as such, is not intended to be a limiting factor of the present invention. Further disclosure of the internal user replaceable battery 110 (not visible due to illustrative limitations) will be provided herein below.

A front surface 115 of the electronics enclosure 45 houses a combination ON/OFF switch and volume control 120 and a sound selector switch 125. The sound selector switch 125 allows the user to control the application of electrical power to the interior electrical components of the apparatus 10 as well as vary the volume level of the playback sounds as produced in the right headphone speaker 50 (as shown in FIG. 1) and the left headphone speaker 60 (as shown in FIG. 1). The volume level would be adjusted to suit user preferences and/or ambient noise levels. The sound selector switch 125 is used by the user 70 (as shown in FIG. 2) to select between different styles of masking sound as produced by the apparatus 10. Such sounds are envisioned to be white noise, the sound of gentle ocean waves, the sound of soft rain, the sound of falling water, the sound of insects at night, the sound of soothing melodic melodies, or the like. The inclusion or exclusion of any particular type of masking/emotionally soothing sound is not intended to be a limiting factor of the present invention.

Figure 4:
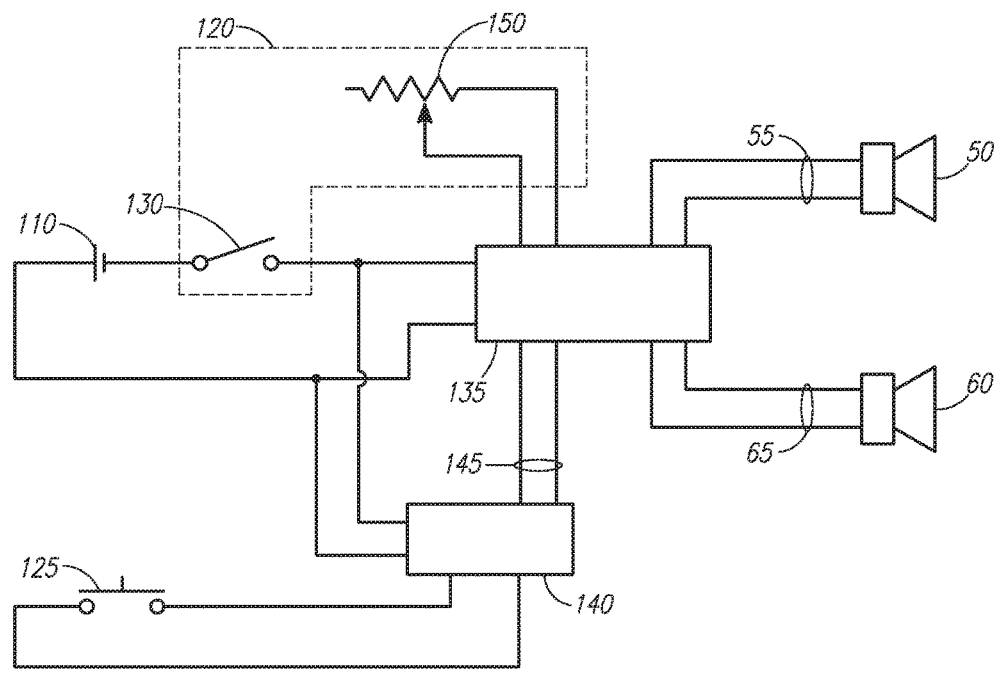

Referring finally to FIG. 4, an electrical block diagram depicting the major electrical components of the apparatus 10, according to the preferred embodiment of the present invention is disclosed. Electrical power from the internal user replaceable battery 110 is routed through a ON/OFF switch portion 130 of the combination ON/OFF switch and volume control 120 where it is passed to an amplifier 135 and a digital sound circuit with internal memory 140 through a parallel electrical connection. The digital sound circuit with internal memory 140 produces an analog circuit waveform which is passed by a connecting circuit path 145 to the input of the amplifier 135. The actual sound pattern that is produced by the digital sound circuit with internal memory 140 is governed by the sound selector switch 125 acting as a simple single pole, spring return pushbutton. Each push of the sound selector switch 125 cycles to the next repeating sound pattern which then repeats in a cyclical manner. The amplifier 135 operates in a conventional manner and amplifies the incoming analog signal on the connecting circuit path 145 to an appropriate level for reproduction by the right headphone speaker 50 and left headphone speaker 60 which is provided by the right headphone cable 55 and the left headphone cable 65 respectively. The output level of the amplifier 135 is controlled by a potentiometer portion 150 of the combination ON/OFF switch and volume control 120.

It is envisioned that other styles and configurations of the present invention can be easily incorporated into the teachings of the present invention, and only one (1) particular configuration shall be shown and described for purposes of clarity and disclosure and not by way of limitation of scope.

The preferred embodiment of the present invention can be utilized by the common user in a simple and effortless manner with little or no training. It is envisioned that the apparatus 10 would be constructed in general accordance with FIG. 1, FIG. 3, and FIG. 4.

Upon initial procurement of the apparatus 10, the user 70 would install an appropriate internal user replaceable battery 110 behind the internal user replaceable battery 110 and verify proper operation. At this point in time, the apparatus 10 is ready for utilization.

To begin the utilization process, the user 70 would first slip the apparatus 10 over their head such that the soft inner surface 25 completely covers their eyes 75, the nose bridge 80 is resting comfortably on their nose 85, and the elastic strap 20 is properly positioned around the rear head area 90 of the user 70. Next, the right headphone speaker 50 and the left headphone speaker 60 are positioned in the respective ear of the user 70 by sense of feel. Said right headphone speaker 50 and left headphone speaker 60 are worn and utilized in a typical manner as expected of any other personal audio listening device. Then the user 70 would activate the apparatus 10 by turning the combination ON/OFF switch and volume control 120 to the ON position. This will begin playback of a first audio signal whereupon the user 70 can adjust the volume level to a suitable level which is not too loud but suitable for masking any outside ambient noise. Finally, the user can select the desired audio signal by repeatedly pressing the sound selector switch 125 until the correct/desired one is reached. At this point in time the user can peacefully relax with both visual and audible masking of ambient light and sound being performed by the apparatus 10. Such masking continues until ceased by the user 70 who deactivates and removes the apparatus 10 by reversing the above described process. This places the apparatus 10 in a state whereupon it can be used again at a future time in a cyclical manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. An eye cover, comprising:
   an eye shield having an inner surface bonded to an outer surface, said eye shield forming a nose bridge;
   an elastic strap having a first end attached to a first side of said eye shield and a second end, said second end opposite the first end, said second end attached to a second side of the eye shield opposite the first end;
   a control device located within a housing mounted on said elastic strap adjacent to a first ear position of said elastic strap, said control device being in electrical communication with a power source located within said housing;
   a first headphone speaker located at said first ear position of said elastic strap, said first headphone speaker in electrical communication with said control device via a first cable connecting said first headphone speaker and said control device; and
   a second headphone speaker located at a second ear position of said elastic strap, said second headphone speaker in electrical communication with said control device via a second cable connecting said second headphone speaker and said control device; and
   said eye shield worn about a face of a user;
   said elastic strap extended around a head of said user;
   a portion of said second cable routed through said elastic strap and said eye shield, between said inner surface and said outer surface, from said second ear position of said elastic strap to said control device such that said portion of said second cable extends over said face of said user;
   said first headphone speaker worn in a first ear of said user and second headphone speaker worn in a second ear of said user; and
   said control device having a plurality of programmed audio data, said control device is operable to selectively playback said programmed audio data through said first headphone speaker and said second headphone speaker;
   further comprising a power switch located on an exterior face of said housing, said power switch in electrical communication between said power source and said control device; and
   further comprising a sound selector switch located on said exterior face of said housing, said sound selector switch in electrical communication between said power source and said control device.

2. The eye cover of claim 1, wherein said inner surface is made of terry cloth or satin.

3. The eye cover of claim 1, wherein each subsequent activation of said sound selector switch cycles through said plurality of programmed audio data.

4. The eye cover of claim 1, further comprising a volume control switch located on said exterior face of said housing, said volume control switch in electrical communication between said power source and each said first headphone speaker and said second headphone speaker.

5. The eye cover of claim 4, wherein said power switch and said volume control switch are combined.

6. The eye cover of claim 1, wherein said plurality of programmed audio data comprises white noise, a plurality of ocean wave sounds, a plurality of rain sounds, a plurality of falling water sounds, a plurality of insect sounds, and a plurality of melodic sounds.

7. An eye cover, comprising:
   an eye shield having a first layer incorporating an inner surface formed from a first layer of a soft inner surface material and a second layer incorporating an outer surface formed from a second layer of a durable outer surface material and a nose bridge, said first layer and said second layer being bonded together;
   a continuous elastic strap having a first end attached to a first side of said eye shield and a second end, opposite the first end, attached to a second side of the eye shield, opposite the first end;
   a control device located within a housing mounted on said elastic strap adjacent to a first ear position of said elastic strap, said control device being in electrical communication with a power source located within said housing;
   a first headphone speaker located at said first ear position of said elastic strap and in electrical communication with said control device via a first cable connecting said first headphone speaker and said control device; and
   a second headphone speaker located at a second ear position of said elastic strap and in electrical communication with said control device via a second cable connecting said second headphone speaker and said control device; and wherein;
   said eye shield worn about a face of a user;
   said elastic strap extended around a head of said user;
   a portion of said second cable routed through said elastic strap and said eye shield, between said first layer and said second layer, from said second ear position of said elastic strap to said control device such that a portion of said second cable extends over said face of said user;
   said first headphone speaker worn in a first ear of said user and second headphone speaker worn in a second ear of said user; and
   wherein said control device having a plurality of programmed audio data and is operable to selectively playback through said first headphone speaker and second headphone speaker;
   further comprising a power switch located on an exterior face of said housing and in electrical communication between said power source and said control device; and
   further comprising a sound selector switch located on said exterior face of said housing and in electrical communication between said power source and said control device, wherein each subsequent activation of said sound selector switch cycles through said plurality of programmed audio data.

8. The eye cover of claim 7, wherein said first layer of said soft material is made of terry cloth or satin.

9. The eye cover of claim 7, further comprising a volume control switch located on said exterior face of said housing and in electrical communication between said power source and each said first headphone speaker and second headphone speaker.

10. The eye cover of claim 9, wherein said power switch and said volume control switch are combined.

11. The eye cover of claim 7, wherein said plurality of programmed audio data comprises white noise, a plurality of ocean wave sounds, a plurality of rain sounds, a plurality of falling water sounds, a plurality of insect sounds, and a plurality of melodic sounds.

* * * * *